United States Patent
Foget et al.

(10) Patent No.: US 8,529,706 B2
(45) Date of Patent: Sep. 10, 2013

(54) METHOD AND APPARATUS FOR CLEANING A MOUTHGUARD

(76) Inventors: Steve Foget, Orleans (CA); Donald S. Cogan, Ottawa (CA)

( * ) Notice: Subject to any disclaimer, the term of this patent is extended or adjusted under 35 U.S.C. 154(b) by 754 days.

(21) Appl. No.: 12/514,920

(22) PCT Filed: Nov. 14, 2007

(86) PCT No.: PCT/CA2007/002012
§ 371 (c)(1),
(2), (4) Date: Aug. 11, 2009

(87) PCT Pub. No.: WO2008/058375
PCT Pub. Date: May 22, 2008

(65) Prior Publication Data
US 2010/0043838 A1   Feb. 25, 2010

(30) Foreign Application Priority Data
Nov. 14, 2006   (CA) .................................... 2567905

(51) Int. Cl.
*B08B 3/04* (2006.01)
(52) U.S. Cl.
USPC ............... 134/26; 134/34; 134/135; 134/200; 206/83
(58) Field of Classification Search
USPC ................ 134/26, 27, 34, 93, 117, 135, 137, 134/200, 201; 206/6.1, 83, 216, 361, 362.2, 206/581; 220/495.01
See application file for complete search history.

(56) References Cited

U.S. PATENT DOCUMENTS

| | | | |
|---|---|---|---|
| 4,724,855 A * | 2/1988 | Jackson et al. | 134/93 |
| 5,275,185 A * | 1/1994 | Florjancic | 134/93 |
| 6,217,933 B1 | 4/2001 | Edwards et al. | |
| 6,343,612 B1 | 2/2002 | Dahl | |
| 6,499,494 B2 * | 12/2002 | Berghash et al. | 134/135 |
| 6,510,877 B1 * | 1/2003 | Trajano et al. | 141/100 |
| 6,705,333 B1 * | 3/2004 | Pourcho | 134/135 |
| 2004/0244805 A1 * | 12/2004 | Cook et al. | 128/859 |

FOREIGN PATENT DOCUMENTS

| | | |
|---|---|---|
| DE | 1 909 545 | 9/1970 |
| EP | 0 535 351 A1 | 4/1993 |

OTHER PUBLICATIONS

International Search Report for International Patent Application No. PCT/CA2007/002012, Canadian Intellectual Property Office, Gatineau, Quebec, Canada, mailed Apr. 7, 2008.

* cited by examiner

*Primary Examiner* — Saeed T Chaudhry
(74) *Attorney, Agent, or Firm* — Sterne, Kessler, Goldstein & Fox P.L.L.C.

(57) ABSTRACT

A device for cleaning and storing a mouthguard, including two main chambers shaped for receiving and holding a mouthguard. One of the main chambers has a sealable lid for retaining disinfecting liquid and the other main chamber has vents to allow water to drain away, and to allow air flow for drying the mouthguard.

17 Claims, 6 Drawing Sheets

METHOD AND APPARATUS FOR CLEANING A MOUTHGUARD

FIELD OF THE INVENTION

The present invention relates generally to devices for cleaning, drying and storing dental appliances such as mouthguards. Specifically, the present invention provides a practical solution to the problem of cleaning and storing mouthguards or other dental appliances in a hygienic fashion between uses.

BACKGROUND OF THE INVENTION

As is the case with any reusable dental appliance, mouthguards need to be cleaned between uses as they could otherwise provide an ideal environment for the reproduction of microbes. A proper cleaning of a mouthguard requires the application of a disinfecting substance, thorough rinsing, and drying.

The present invention aims to provide a solution to this problem, by disclosing a multi-chambered container. At least one chamber is suited for the application of a disinfecting substance, while another is suited for rinsing and drying.

There are a number of containers for mouthguards or other dental appliances known in the prior art.

U.S. Pat. No. 5,203,351 to Adell teaches a single-chamber mouthguard container with two possible "closed" positions, allowing some mouthguards to remain attached to a helmet through an attaching strap, while being enclosed in the container.

U.S. Pat. No. 5,323,787 to Pratt discloses a single-chamber dental appliance container with a grid pattern projecting from the bottom wall, allowing the dental appliance to completely soak in a cleansing liquid.

U.S. Patent Application No. 2004/0244805 to Cook et al. teaches a single-chamber mouthguard container with a set of ribs projecting from the bottom wall, defining a generally u-shaped opening to securely store the mouthguard and providing a plurality of vent apertures to allow air circulation. Cook et al. further teaches that the mouthguard case be impregnated with an antimicrobial agent as disclosed in U.S. Pat. No. 6,553,996.

U.S. Pat. No. 5,298,077 to Saarela et al. discloses a single-chamber cleaning device for a dental appliance, such as dentures, comprising two circular pieces, each having a plurality of bristles extending inwardly and a plurality of slots. The two pieces rotatably engage each other, allowing the user to scrub the dental appliance. Meanwhile, the slots allow the user to rinse the dental appliance under water from inside the container.

U.S. Pat. No. 2,102,643 to Pellegrini discloses a dual-chambered cleaning device for a dental appliance. However, the two chambers are used for storing upper and lower dentures separately, and a central aperture between the two chambers allows for fluid to flow from one chamber to another.

Therefore, there is a need for a dual-chambered cleaning device for dental appliances, such as mouthguards, one chamber providing the appropriate environment for the cleaning step and the other for rinsing, drying and storage.

SUMMARY OF THE INVENTION

The present invention provides a container comprising at least two separate chambers, each of them shaped to hold a mouthguard or any other dental appliance of a similar nature.

The first chamber, when closed, is hermetically sealed, to contain a cleaning/disinfecting fluid to be applied to the mouthguard. In one embodiment of the present invention, the first chamber can include a false bottom with vents so that the false bottom is in fluid communication with the first chamber, allowing the user to securely place a disinfecting tablet in the false bottom. As disinfecting tablets typically produce gas when dissolved in water, the first chamber includes, according to a preferred embodiment, one or more pinhole sized apertures which allow gas to escape but preventing all but an insignificant amount of liquid from leaking. Alternatively, the first chamber can include a pressure relief valve.

The second chamber includes a plurality of vents preferably on its top, bottom, and side surfaces, allowing the mouthguard to be thoroughly rinsed from within the container, and to provide sufficient air circulation so that the mouthguard can dry rapidly enough to inhibit the growth of microorganisms on its surface. According to one embodiment of the present invention, the second chamber has a plurality of ribs on its bottom wall, allowing air to circulate around the entire surface of the mouthguard during the drying phase.

It is therefore an object of the present invention to provide a practical solution to the problem of cleaning and storing a mouthguard or other similar dental appliances.

It is a further object in a preferred embodiment of the present invention to provide a dual-chambered cleaning device for mouthguards allowing for the proper disinfecting, rinsing and drying of a mouthguard.

It is a further object in a preferred embodiment of the present invention to provide a dual-chambered cleaning device for mouthguards, which is easy to use, and which requires a minimum of effort, so that young children can operate it with little difficulty.

According to the present invention then, there is provided a device for storing and cleaning a dental appliance comprising a first chamber for at least partially immersing said appliance in a cleaning fluid, defined by a bottom wall, and a sidewall and a lid, said lid having means to sealingly close the chamber; a second chamber for draining and drying said appliance, defined by a bottom wall, a sidewall and a lid, said lid having means to remain shut, at least one of said bottom wall, sidewall and lid having one or more of apertures formed therethrough for the drainage of fluid and the circulation of air.

BRIEF DESCRIPTION OF THE DRAWINGS

Preferred embodiments of the present invention will now be described in greater detail and will be better understood when read in conjunction with the following drawings in which.

DETAILED DESCRIPTION OF THE PREFERRED EMBODIMENT

Figure 1:
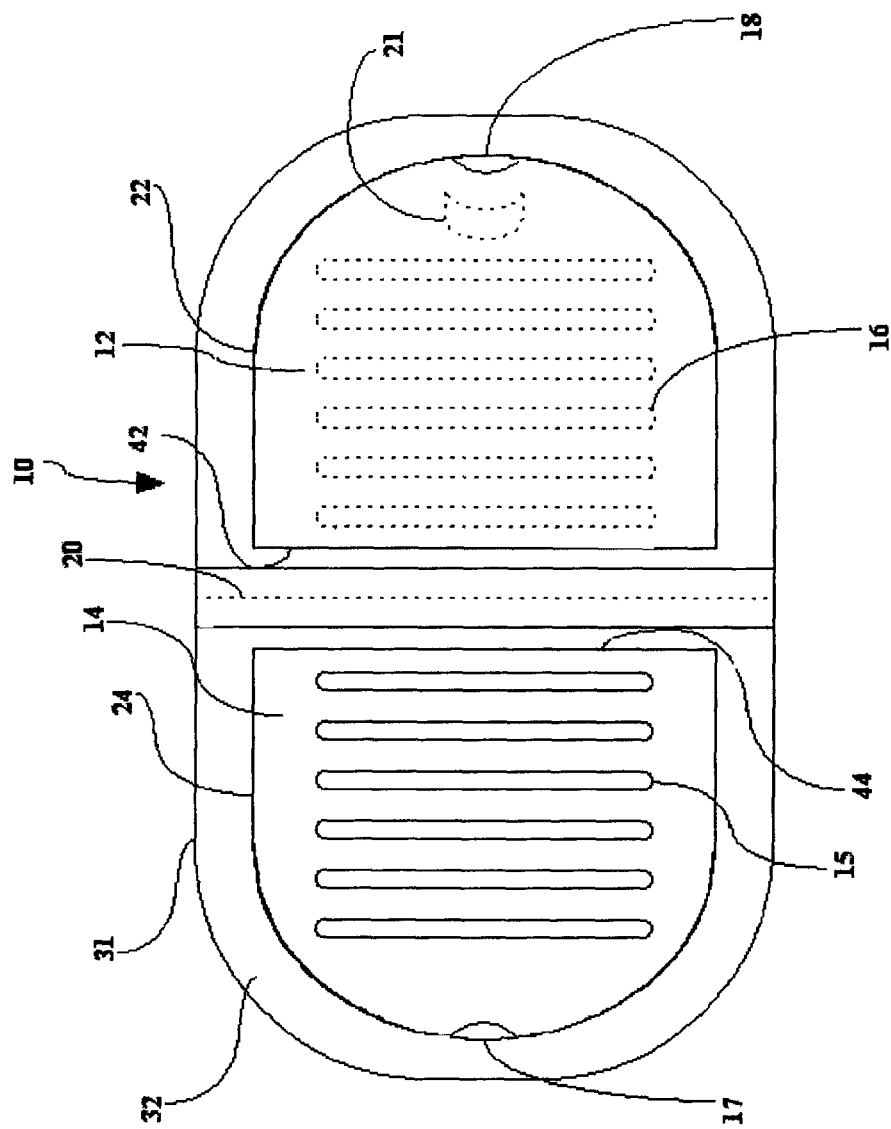
FIG. 1 is a top plan view of a device in accordance with the present invention.
Figure 2:
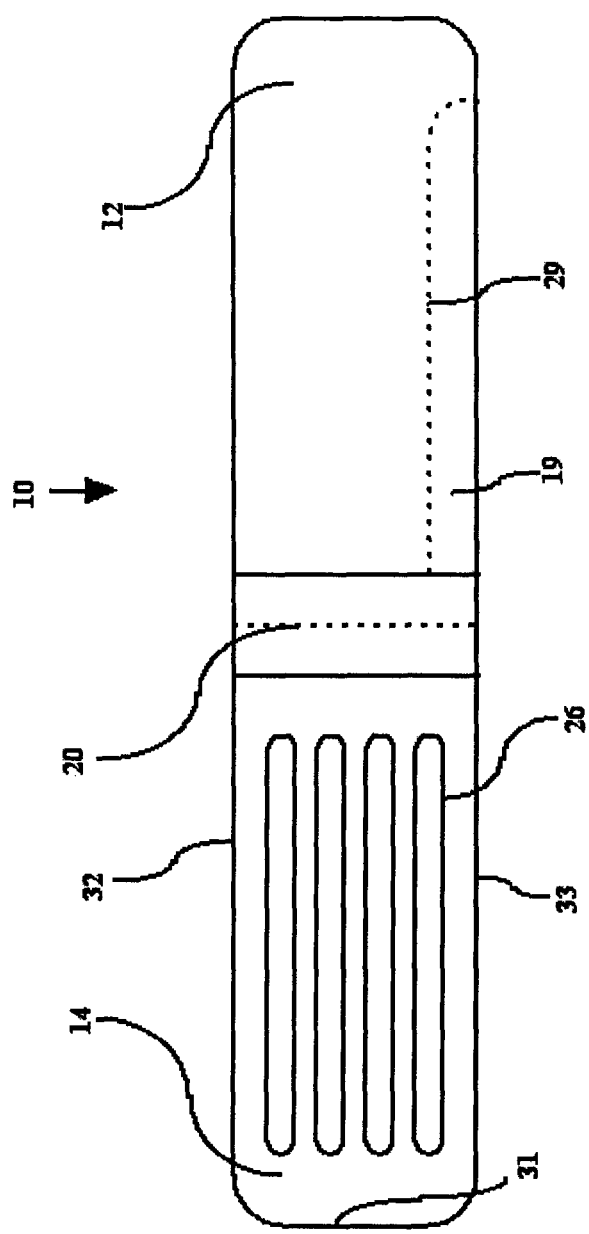
FIG. 2 is a side elevational view of a device in accordance with the present invention.

Referring to FIGS. 1 and 2, there is shown the present device 10 in the nature of a two-chambered mouthguard or other appliance holder. The holder 10 is bounded by a peripheral sidewall 31, a top wall 32, and a bottom wall 33. Dividing the device into two chambers 12 and 14 is a vertical wall 20, projecting from bottom wall 33 to top wall 32.

The chambers 12 and 14 are each defined by sidewall 31, vertical wall 20, top wall 32, and lids 22 and 24. Lids 22 and 24 are hingedly connected to top wall 32 at 42 and 44 respectively. The hinged connection may consist of a thinning out of the construction material, such as plastic, so as to create a flexible strip of material, or by other means known in the art.

Lid 22, when closed, creates a tight enough seal to prevent liquid, such as a cleaning and/or disinfecting solution, from escaping first chamber 12. The lid is held shut by a clip 18 in top wall 32 for example, or by any other means known in the art, such as a tongue and groove snap fit.

Referring to FIG. 2, according to one embodiment of the present invention, first chamber 12 includes a false bottom 19, with a lid 29 covering most of the surface of bottom wall 33 underlying first chamber 12. Lid 29 is formed with a plurality of vents 16 and a clip 21 used to hold it shut.

Lid 24 can be formed with a plurality of vents 15 allowing air to circulate in chamber 14. A clip 17 is provided allowing lid 24 to snap shut into top wall 32.

During operation, the user would first place the mouthguard in first chamber 12 along with an appropriate amount of a cleaning and/or disinfecting liquid or substance, and close lid 22. The user can then either shake the device to agitate the mouthguard, or leave the mouthguard to soak in the disinfecting liquid. Once the user is satisfied the mouthguard has been sufficiently treated, it can be removed and placed into second chamber 14. Lid 24 is closed and the user can then choose to rinse the mouthguard by running water over the vents 15 of lid 24, and allowing the water to escape through vents 26 in the sidewall or similar vents in bottom wall 33, or vice versa, or the residual fluid on the mouthguard can simply be allowed to drain through the vents. The user can then leave the mouthguard to dry in the holder in any well ventilated place.

If the holder includes false bottom 19, the user would lift lid 29 and load the false bottom with a disinfecting tablet, such as Polident™. The mouthguard would then be dropped in and chamber 12 can be filled with bottled or tap water. Lid 22 is closed and user can then either agitate the device by shaking it, or allow the dissolving action of the tablet to do the cleansing. This feature allows parents to safely and easily help their children keep their mouthguards clean without the need for the children themselves to handle the disinfecting tablet if the child is particularly young.

Figure 3:
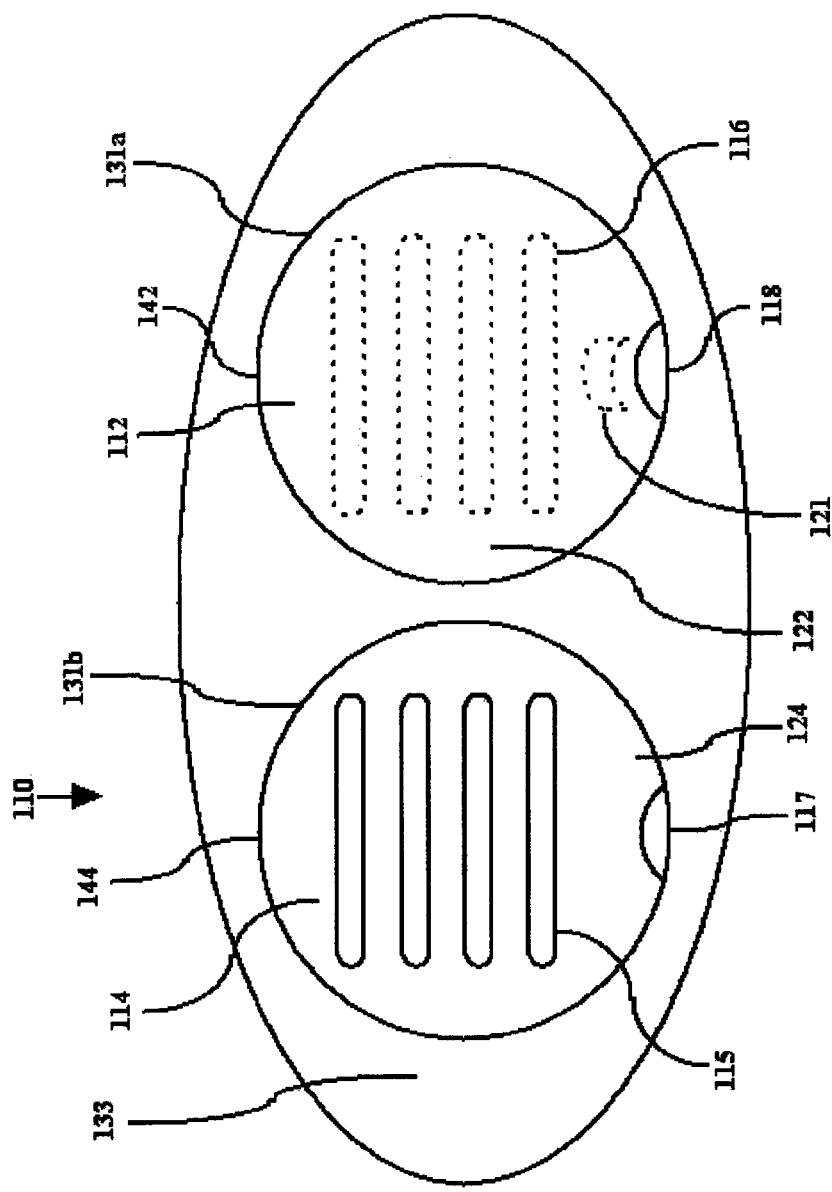
FIG. 3 is a top plan view of a device in accordance with another embodiment of the present invention.

Referring to FIG. 3, another embodiment of the holder is generally indicated by reference numeral 110. First chamber 112 and second chamber 114 extend from bottom wall 133, which also acts as a base for the device. Chambers 112 and 114 are defined by bottom wall 133, respective sidewalls 131a and 131b, and lids 122, and 124. Lids 122 and 124 can be screw tops, or, to prevent loss, they can be hingedly connected to sidewalls 131a and 131b, at 142 and 144, respectively.

If lid 122 is hinged, it can be closed using clip 118 to create a tight enough seal to prevent liquid from escaping, even when the device is shaken.

Lid 124 can be securely shut using clip 117. The lid, side wall 131b and/or bottom wall 133 defining drying chamber 114 and can be formed with a plurality of vent apertures 115 to promote drainage and drying of the appliance.

Figure 4:
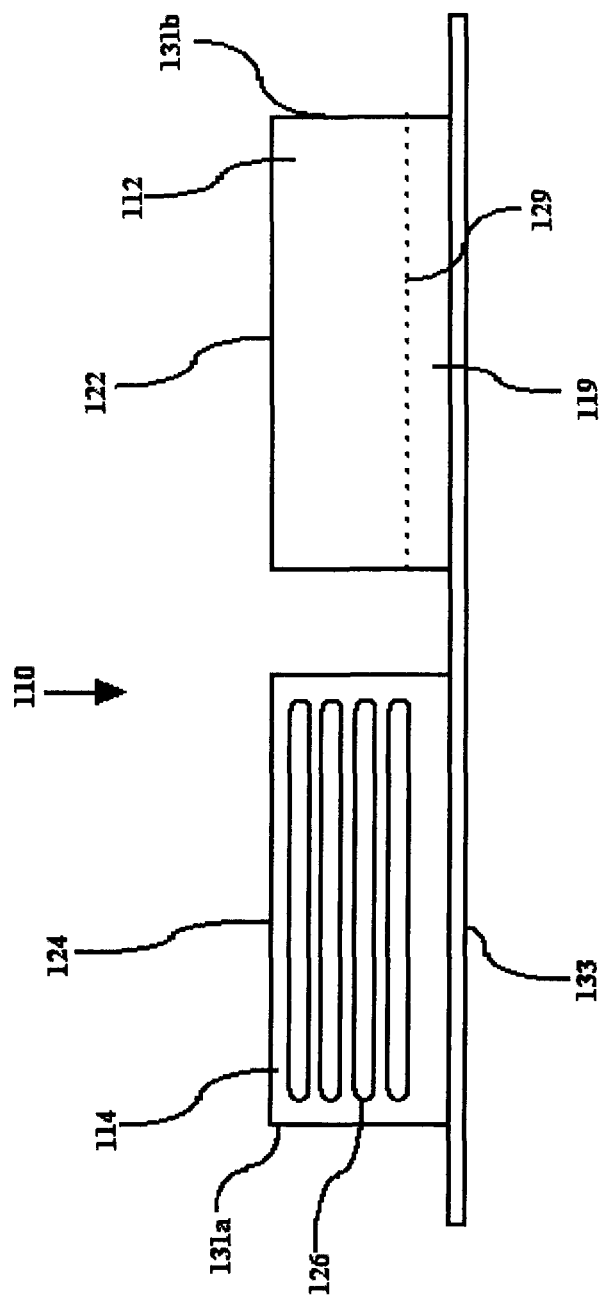
FIG. 4 is a side elevational view of a device in accordance with another embodiment of the present invention.

Referring to FIG. 4, first chamber 112 can include a false bottom 119, with a lid 129, having a plurality of vents 116 and a clip 121 allowing the lid to be opened and snapped shut.

In function, this embodiment is used and works in the same manner as the embodiment described above with reference to FIGS. 1 and 2.

Figure 5:
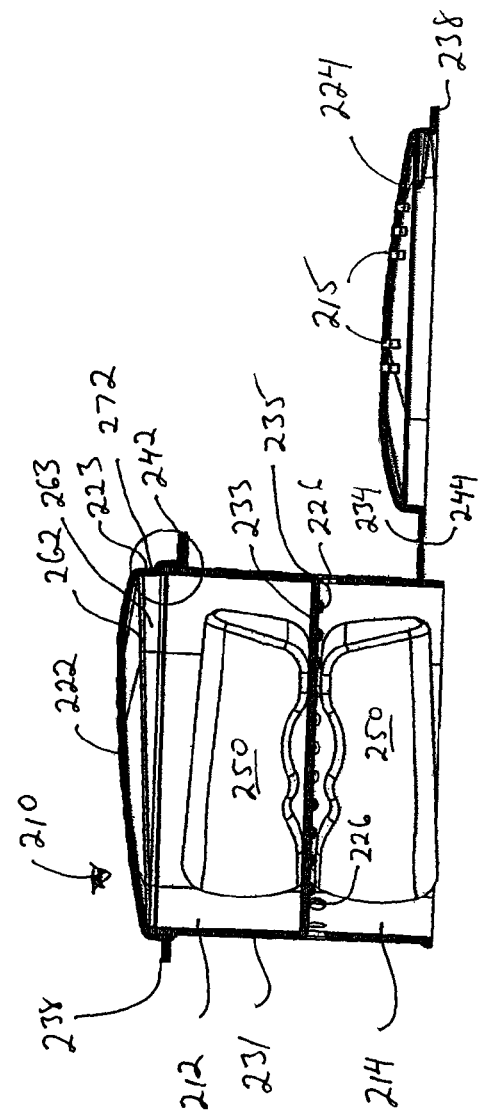
FIG. 5 is a cross-sectional view of a device in accordance with yet another embodiment of the present invention.

Referring to FIG. 5, yet another embodiment of the present invention is shown generally indicated by reference numeral 210. This is a double clam shell configuration. First chamber 212 and second chamber 214 share a common bottom wall 233 in a back-to-back configuration, and sidewall 231 extends from both sides of bottom wall 233, thereby defining both chambers.

Both chambers 212 and 214 are further defined by lids 222 and 224, respectively hingedly connected to side wall 231 by hinges 242 and 244.

Figure 6:
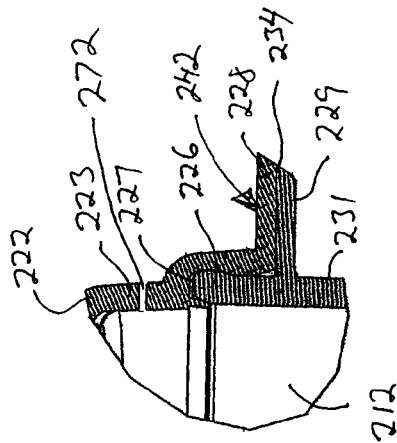
FIG. 6 is a close-up view of the hermetic seal in accordance with yet another embodiment of the present invention.

The lids snap fit to the outer peripheral edges of side wall 231. Reference is made to FIG. 6 in this regard. The outer peripheral edges of side wall 231 are formed with a slightly enlarged bead 226 which snap fits into a correspondingly shaped groove 227 that extends around the inner periphery of the lids. This connection provides a relatively strong and fluid tight seal to prevent leakage from chamber 212 in particular and to resist the lid being popped off by the pressure of gas released when cleansing tablets are dissolved. As will be appreciated, drying chamber 214 is not subject to the same internal pressures and of course the drainage of fluid is actually required, so lid 224 does not require the same closure and sealing mechanism as lid 222. A simple friction fit between the lid and the side wall will suffice.

Each of lids 222 and 224 are provided with outwardly extending tabs 238 that can be used to more easily open the lids.

Figure 8:
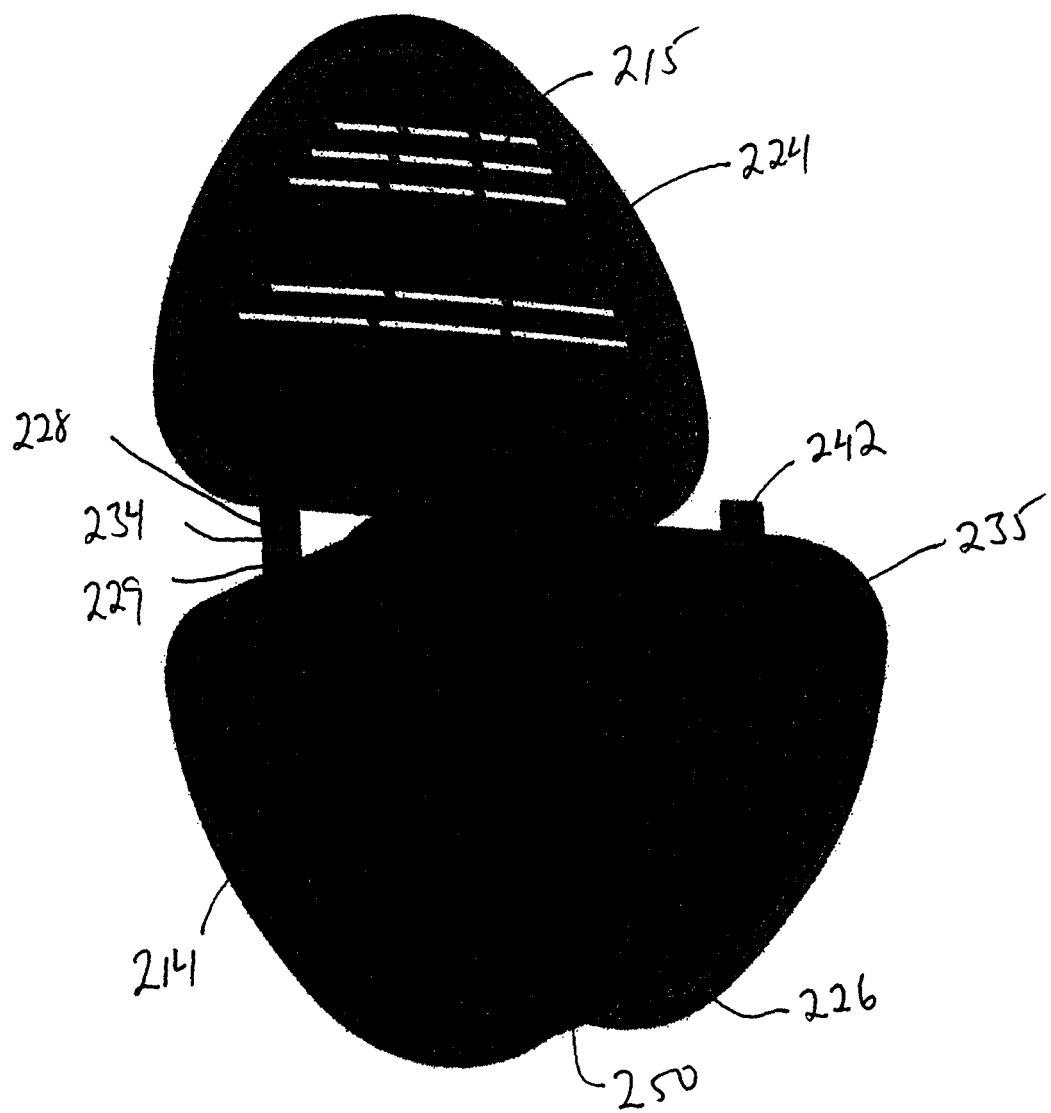
FIG. 8 is a perspective view of the device shown in FIG. 5.

Lid 224 for the drying chamber includes a plurality of venting apertures 215 which may be in the nature of parallel, spaced apart slots best seen in FIG. 8 that extend through the lid for the ingress and egress of air and fluid. The side wall 231 around the drying chamber is also preferably perforated with a plurality of holes or slots 226 immediately adjacent bottom wall 233 as shown in FIGS. 5 and 6 to promote drainage and the circulation of air.

In FIG. 5, a mouthguard 250 is shown in each of chambers 212 and 214, one being cleaned while the other is being dried or simply stored. The surface of bottom wall 233 facing into second chamber 214 can include a plurality of parallel, spaced apart ribs 235, allowing the mouthguard to rest or be spaced slightly above bottom wall 233, thereby allowing air and liquid to circulate all around the mouthguard for a more efficient draining and drying phase. It will be seen as well that cleaning chamber 212 does not have a false bottom. If a cleansing tablet is used, it can simply be dropped into the chamber before or after the water has been added. A false bottom can be utilized if desired however.

With reference to FIG. 6, each of hinges 242/244 comprises a tab 229 extending from side wall 231 and opposing tab 228 extending from lids 222/224. The two tabs are joined at their opposed outer edges by a relatively thin flexible web 234 of the same material forming the tabs, which will typically be a plastic material, that allows the tabs to rotate relative to each other. The tabs allow the hinges the necessary clearance to open and close relative to bead 226 so that groove 227 compressibly seals against the bead in a secure and relatively fluid tight snap fit.

Figure 7:
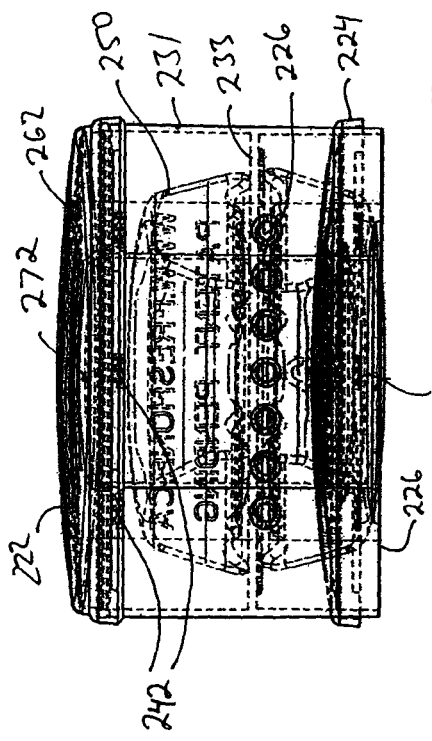
FIG. 7 is a side elevational view of a device in accordance with yet another embodiment of the present invention.

Referring to FIGS. 5, 6 and 7, the present holder can include some adaptations to facilitate its use with cleaning tablets.

As discussed above, it is contemplated that the present invention can be used in conjunction with different cleaning agents, including disinfecting tablets which dissolve in water. Such tablets produce gas when used, and therefore a perfectly hermetic seal between lid 222 and side wall 231 may be unsuitable as the pressure buildup could force the seal, causing it to leak or even pop open, spilling the chamber's contents.

One adaptation to deal with this is to increase the volume of chamber 212 above its maximum fill line, which is the top of side wall 231. This can be done by adding a bulge 262 to lid 222. In FIG. 5, the bulge is in the form of an added wedge 263 of volume but the same effect can be achieved by making the lid more dome shaped or by increasing the height of the lid's side wall 223 (FIG. 6).

Another adaptation which can be used by itself or in addition to the enlargement of lid 222 is to form the lid with one or more very small pinholes 272. The hole or holes can be formed in the lid where shown in FIGS. 5 and 7 or anywhere else in the lid that will normally be above the chamber's fill line. The pinholes are sized so that gas may escape, thereby preventing pressure buildup, but preventing all but a minute amount of liquid to leak. Alternatively, a pressure release valve can be added into the lid or even into side wall 231 of first chamber 212.

In use, mouthguard 250 is placed in chamber 212 which is filled with water or some other cleaning fluid. A cleaning tablet can be added, the lid closed and the whole device agitated to promote better cleaning. When cleaning is done, the fluid is dumped from the cleaning chamber and the mouthguard is placed into chamber 214. Added rinsing can be effected under a flow of water, or the mouthguard can be simply be left to naturally drain and dry until needed again.

The foregoing is considered as illustrative only of the principles of the invention. Since numerous modifications will readily occur to those skilled in the art, it is understood that modifications and equivalents may be resorted to, without escaping from the scope of the present invention.

The invention claimed is:

1. A device for storing and cleaning a dental appliance comprising: a first chamber for at least partially immersing said appliance in a cleaning fluid, defined by a bottom wall, and a sidewall and a lid, said lid having means to sealingly close the chamber; a second chamber for draining and drying said appliance, defined by a bottom wall, a sidewall and a lid, said lid having means to remain shut, at least one of said bottom wall, sidewall and lid having one or more of apertures formed therethrough for the drainage of fluid and the circulation of air, wherein the first chamber further comprises a false bottom defined by an interior lid disposed within the first chamber and further defined by the bottom wall of said first chamber, said interior lid having means to remain shut, said interior lid further having a plurality of apertures allowing for fluid communication between said false bottom and said first chamber.

2. A device for storing a dental appliance according to claim 1, wherein said first chamber and said second chamber share a portion of their respective sidewall.

3. A device for storing and cleaning a dental appliance according to claim 1, wherein both said first and second chambers are formed on said bottom wall, said bottom wall acting as a base, and wherein both said first and second chambers have separate sidewalls.

4. A device for storing and cleaning a dental appliance according to claim 1, wherein said first and said second chamber are u-shaped, so as to resemble the shape of most dental appliances.

5. A device for storing and cleaning a dental appliance according to claim 1, wherein the sidewall of said second chamber is formed with a plurality of apertures extending therethrough for draining and venting.

6. A device for storing and cleaning a dental appliance according claim 1, wherein said first chamber and said second chamber share said bottom wall to be in back-to-back configuration.

7. A device for storing and cleaning a dental appliance according to claim 1, wherein the means to sealingly close the first chamber comprise a peripherally extending bead on an outer edge of said sidewall of said first chamber, and an opposed correspondingly shaped and co-operating groove in a peripheral edge of said lid of said first chamber, said groove engaging said bead in a compressive fluid sealing snap fit.

8. A device for storing and cleaning a dental appliance according to claim 1, wherein an inside surface of said bottom wall of said second chamber has raised ribs thereon to facilitate draining and drying of said dental appliance.

9. A device for storing and cleaning a dental appliance according to claim 1, wherein said first chamber has pinhole sized apertures formed therein for the escape of a gas.

10. A device for storing and cleaning a dental appliance according to claim 9, wherein said pinhole sized apertures are formed in said lid of said first chamber.

11. A device for storing and cleaning a dental appliance according to claim 1, wherein said first chamber includes a pressure release valve for the escape of gas.

12. A device for storing and cleaning a dental appliance according to claim 11, wherein said pressure release valve is located in the lid of said first chamber.

13. A device for storing and cleaning a dental appliance according to claim 5, wherein at least some of said plurality of apertures on said sidewall of said second chamber are aligned to drain fluid from said bottom wall of said second chamber.

14. A device for storing and cleaning a dental appliance according to claim 1, wherein the lid of said first chamber is shaped to increase the volume of said first chamber when said lid is in a closed position thereof.

15. A method of cleaning a dental appliance, comprising: placing said appliance in a first chamber for immersion in a cleaning fluid, said first chamber being defined by a bottom wall, a side wall and a lid, said lid being adapted to sealingly close said first chamber, said first chamber further comprising a false bottom defined by an interior lid disposed within the first chamber and further defined by the bottom wall of said first chamber, said interior lid having means to remain shut, said interior lid further having a plurality of apertures allowing for fluid communication between said false bottom and said first chamber; and after cleaning said appliance in said first chamber, removing the appliance therefrom and placing it into a second chamber for draining and drying the appliance, the second chamber being connected to said first chamber by at least one common wall, said second chamber being defined by a bottom wall, a side wall and a lid, the lid having means to close the second chamber, at least one or more of said bottom wall, side wall and lid having one or more apertures formed therethrough for the drainage of fluid and the circulation of air.

16. The method of claim 15 further comprising adding a cleaning agent to said first chamber for enhanced cleaning or disinfection of the dental appliance, the cleaning agent added into the false bottom.

17. The method of claim 16 wherein said cleaning agent is a tablet soluble in the cleaning fluid in said first chamber to release cleaning or disinfecting agents.

* * * * *